United States Patent
Duffy et al.

(10) Patent No.: US 6,333,082 B1
(45) Date of Patent: *Dec. 25, 2001

(54) LIQUID CRYSTALLINE (E,E)-BUTADIENE COMPOUNDS AND MIXTURES AND DEVICES CONTAINING SUCH COMPOUNDS

(75) Inventors: Warren L Duffy; John W Goodby; Stephen M Kelly, all of Hull (GB)

(73) Assignee: QinetiQ Ltd, London (GB)

( * ) Notice: Subject to any disclaimer, the term of this patent is extended or adjusted under 35 U.S.C. 154(b) by 0 days.

This patent is subject to a terminal disclaimer.

(21) Appl. No.: 09/607,959

(22) Filed: Jun. 30, 2000

Related U.S. Application Data

(62) Division of application No. 09/147,886, filed as application No. PCT/GB97/02542 on Sep. 22, 1997, now Pat. No. 6,106,908.

(30) Foreign Application Priority Data

Sep. 26, 1996 (GB) .................................................. 9620061

(51) Int. Cl.$^7$ ......................... C09K 19/34; C07C 43/188; C07D 333/08; C07D 213/30; C07D 239/02; C07D 319/06

(52) U.S. Cl. ................. 428/1.1; 252/299.61; 252/299.63; 252/299.66; 252/299.67; 544/242; 544/298; 544/335; 546/339; 546/340; 546/341; 548/136; 549/80; 549/83; 549/369

(58) Field of Search ......................... 252/299.61, 299.63, 252/299.66, 299.67; 428/1.1; 544/242, 298, 335; 546/339, 340, 341; 548/136; 549/369, 29, 61, 62, 64, 80, 83; 568/657, 667

(56) References Cited

U.S. PATENT DOCUMENTS

| | | | |
|---|---|---|---|
| 5,449,810 | * 9/1995 | Fujita et al. | 558/425 |
| 5,609,791 | * 3/1997 | Fujits et al. | 252/299.63 |
| 5,662,830 | * 9/1997 | Fujita et al. | 252/299.63 |
| 5,976,408 | * 11/1999 | Fujita et al. | 252/299.63 |
| 6,106,908 | * 8/2000 | Duffy et al. | 428/1.1 |

FOREIGN PATENT DOCUMENTS 08-59556 * 3/1996 (JP) .

OTHER PUBLICATIONS

Chemical Abstracts, vol. 125, No. 6, Aug. 5, 1996, Columbus, Ohio, US; abstract No. 072143, Sakamaki Y et al: Hexadienoyloxybenzoic acid phenolic compound ester and liquid crystal composition XP002050221 see abstract & JP 08 059 556 A (Citizen Watch Co Ltd; Japan) Mar. 5, 1996.

Chemical Abstracts, vol. 113, No. 14, Oct. 1, 1990, Columbus, Ohio, US; abstract No. 124013, Shibata T et al: "2–'4–(2–7–Octadienyloxy)phenyl!–5–alkylpy rimidines as liquid crystals" XP002050222 see abstract & JP 09 062 865* (Adeka Argus Chemical Co., Ltd.; Japan).

Kelly S M: "The effect of the position and configuration of carbon–carbon double bonds on the mesomorphism of thermotropic, non–amphiphilic liquid crystals" Liq. Cryst. (LICRE6,02678292):96; vol. 20 (5); pp. 493–515, Hull Univ.;Sch. Chem.; Hull; HU6 7RX; UK (GB), XP002050219 see the whole document.

Kurihara S et al: "Polymerization of liquid crystalline monomers with diene groups and formation of polymer network with uniaxial molecular alignment" J. Appl. Polym. Sci. 9JAPNAB, 00218995);96; vol. 61 (2); pp .279–283, Kumamoto University; Faculty Engineering; Kumamoto; 860; JAPAN (JP), XP002050220 see the whole document.

* cited by examiner

Primary Examiner—Shean C. Wu
(74) Attorney, Agent, or Firm—Nixon & Vanderhye

(57) ABSTRACT

Liquid crystalline compounds useful in super twisted nematic liquid crystal displays are described and have the formula:

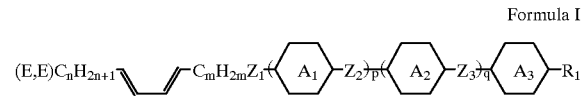

Formula I wherein n is 1–5;

m is 0–5;

p is 0, 1 or 2;

q is 0, 1 or 2 p+q is less than or equal to 3;

$A_1$, $A_2$, $A_3$ are independently chosen from 1,4-disubstituted benzene, 2,5-disubstituted pyrimidine, 1,5-disubstituted pyridine, 2,6-disubstituted naphthalene which may be laterally substituted with F, Cl, Br or CN, trans-1,4-disubstituted cyclohexane, 2,5-disubstituted dioxane, 2,5-disubstituted thiophene, 2,5-disubstituted furan, 2,5-disubstituted thiodiazole $Z_1$ may be COO, OOC, OCH$_2$, O;

$Z_2$, $Z_3$ are independently chosen from a direct bond, COO, OOC, $C_2H_4$, CH$_2$O, OCH$_2$, $C_4H_8$, $C_3H_6O$, (E)—CH═CHC$_2$H$_4$, (E)—CH═CHCH$_2$O, —C≡C—;

$R_1$ is alkyl, and may contain up to 20 carbon atoms and may be branched or a straight chain; provided that at least one of, $A_1$, $A_2$, $A_3$ is selected from 1,4-disubstituted thiophene.

9 Claims, 1 Drawing Sheet

LIQUID CRYSTALLINE (E,E)-BUTADIENE COMPOUNDS AND MIXTURES AND DEVICES CONTAINING SUCH COMPOUNDS

This application is a division of Ser. No. 09/147,886, filed Mar. 19, 1999, now U.S. Pat. No. 6,106,908 which is a 35 U.S.C. 371 of PCT/GB97/02542 filed Sep. 22, 1997.

The present invention describes new compounds. In particular it describes compounds for use in liquid crystal mixtures and in liquid crystal displays (LCDs) or in applications relating to inter alia thermography utilising nematic liquid crystal or chiral nematic liquid crystal mixtures.

BACKGROUND OF THE INVENTION

LCDs, such as multiplexed Twisted Nematic TN-LCDs, Super Twisted Nematic STN-LCDs, Super Birefringent SBE-LCDs, Electrically Controlled Birefringence ECB-LCDs, or flexoelectric LCDs are currently used or being developed for computer monitors, laptop or notebook computers, portable telephones, personal digital assistants, etc. The optical, electrical and temporal performance, e.g., contrast, threshold and driving voltages, and response times, of such displays depends crucially on the ratios of the elastic constants ($k_{33}$, $k_{22}$, $k_{11}$) and the cell gap, d. Currently commercially available nematic mixtures for sophisticated high-information-content LCDs, such as STN-LCDs, incorporate trans-1,4-disubstituted-cyclohexyl derivatives with a terminal alkenyl chain (i.e., incorporating a carbon-carbon double bond) directly attached to the cyclohexane ring in order to produce the necessary elastic constant ratios for short response times, high multiplexing rates and low driving voltages. Such materials are costly and difficult to synthesise due to the requirement for a trans configuration of the 1,4-disubstituted cyclohexane ring and the necessity of synthesising the carbon-carbon double bond stepwise from this trans-1,4-disubstituted-cyclohexyl intermediate. If the carbon-carbon double bond is substituted at both carbon atoms, it must have a trans (E) configuration in order to exhibit an advantageous combination of elastic constants and to have an acceptably high nematic-isotropic transition temperature (N-I). The trans configuration is then generally produced by isomerisation of the cis (Z) form generated by the preceding Wittig reaction. These materials exhibit low or intermediate values of birefringence ($\Delta n$) due to the presence of the saturated cyclohexane rings. As the ratio $d.\Delta n$ determines the optical properties of TN-LCDs and is fixed for driving the LCD in the first or second minimum, it is clear that higher values of $\Delta n$ would allow smaller cell gaps. As the response time, $t_{on}$ of TN-LCDs is inversely proportional to $d^2$, smaller cell gaps have a dramatic effect on $t_{on}$. Low values of $t_{on}$ also allow the use of colour or more shades of colour due to the shorter frame times.

Liquid crystals with a (E, E)-butadiene chain are known and are described in, for example W. Meier and K. Markau Z. Phys. Chem. N. F., (1961), Vol. 28, pp 190, Y. Goto and T. Ogawa, EPA 0 280 902 (1988).

For all the above applications it is not usual for a single compound to exhibit all of the properties highlighted, normally mixtures of compounds are used which when mixed together induce the desired phases and required properties.

DETAILED DESCRIPTION OF THE INVENTION

Figure 1:
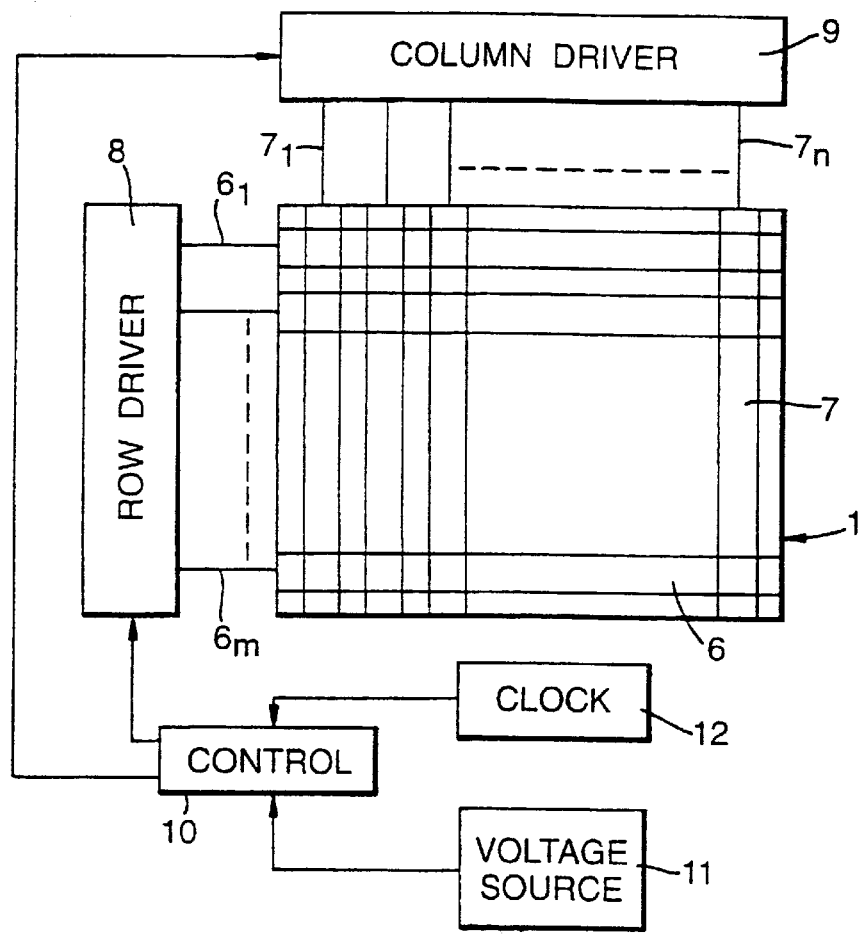
FIG. 1 is a plan view of a matrix multiplex addressed liquid crystal display.

According to this invention materials are provided of Formula I:

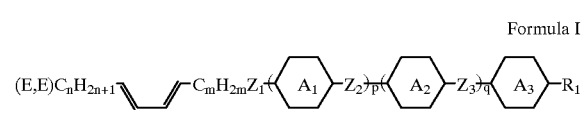

Formula I wherein n may be 1–5;

m may be 1–5;

p may be 0, 1 or 2;

q may be 0, 1 or 2;

p+q is less than or equal to 3;

$A_1$, $A_{21}$ $A_3$ are independently chosen from 1,4-disubstituted benzene, 2,5-disubstituted pyrimidine, 2,5-disubstituted pyridine, 2,6-disubstituted naphthalene which may be laterally substituted with F, Cl, Br or CN, trans-1,4-disubstituted cyclohexane, 2,5-disubstituted dioxane, 2,5-disubstituted thiophene, 2,5-disubstituted furan, 2,5-disubstituted thiodiazole;

$Z_1$ may be COO, OCC, $OCH_2$, O;

$Z_2$, $Z_3$ are independently chosen from a direct bond, COO, OOC, $C_2H_4$, $CH_2O$, $OCH_2$, $C_4H_8$, $C_3H_6O$, (E)—CH=CH$C_2H_4$, (E)—CH=CH$CH_2O$, —C≡C—;

$R_1$ may be alkyl, alkoxy, alkenyl, alkenyloxy, alkanoyl, alkenoyl, F, Cl, Br, CN, $OCHF_2$, $OC_wF_{2w+1}$, NCS or CH=C(CN)$_2$, CH=CF$_2$, (E)—CH=CHCl; $R_1$ may contain up to 20 carbon atoms and may be branched or a straight chain and w may be 1–7.

The structural and other preferences are expressed below on the basis of inter alia desirable liquid crystalline characteristics, in particular an advantageous combination of elastic constants and high birefringence in the nematic phase, a wide nematic phase, a high nematic-isotropic liquid transition temperature and ready synthesis from commercially available. Starting materials already incorporating at least one carbon-carbon double bond with the desired configuration and position.

Preferably n is 1–3;

Preferably when $Z_1$ is 0 m is 1 and when $Z_1$ is COO m is 0;

Preferably n+m is≦5;

Preferably p is 0 or 1;

Preferably q is 0 or 1;

Preferably p+q is 0 or 1;

Preferably $A_1$, $A_2$. $A_3$, are 1,4-disubstituted benzene or trans-1,4-disubstituted cyclohexane;

Preferably $Z_2$, $Z_3$ are direct bonds or $C_2H_4$;

Preferably $R_1$ is nitrile or alkyl or alkoxy.

Overall preferred structures for formula I are those listed below:

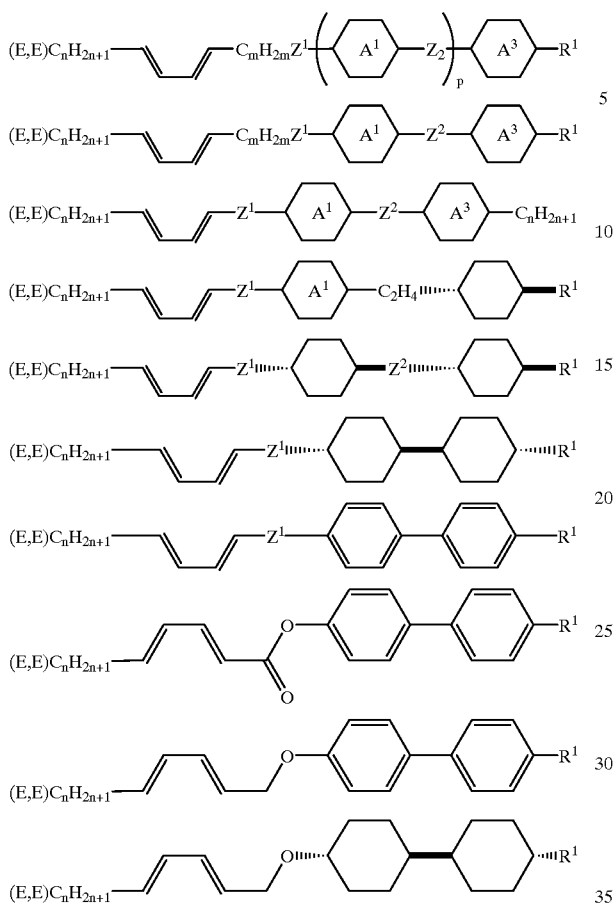

Compounds of formula I can be prepared by various routes. Typically the ethers can be prepared by the Mitsunobu reaction (Synthesis, (1981) pp 1) of a phenol with an alka-2,4-dienol in the presence of triphenyl phosphine, a dehydrating agent, such as diethyl azodicarboxylate, and a suitable solvent, such as tetrahydrofuran or N,N'-dimethylformamide. Alternatively they can be synthesised by alkylation of a secondary alcohol or phenol with the tosylate of the appropriate alka-2,4-dienol in the presence of a suitable base, such as potassium tert.-butoxide, and a suitable solvent, such as tert.-butyl-methyl ether or 1,2-dimethoxyethane (J. Mater. Chem., (1994) Vol. 4, pp 1673). The esters can be prepared by esterification (Angewandte Chemie (1978) Vol. 90, pp 556) of the appropriate phenol or secondary alcohol with an alkenoic acid in the presence of 4-(dimethylamino)pyridine, a dehydrating agent, such as N,N'-dicyclohexylcarbodiimide, and a suitable solvent, such as dichloromethane or N, N'-dimethylformamide. Alternatively they can be synthesised by esterification of the appropriate phenol or secondary alcohol with an alkenoic acid chloride (produced, for example, from the corresponding alkenoic acid by the action of thionyl chloride or oxalyl chloride) in the presence of a base, such as pyridine or triethylamine, and a suitable solvent, such as toluene or dichloromethane.

In the following examples C signifies the crystalline state, N the nematic phase, I the isotropic phase, S the smectic phase and $\Delta T_{NI}$ the temperature range of the nematic phase.

The invention will now be described, by way of example only, with reference to the following examples.

EXAMPLE 1

Preparation of 4-Cyano-4'-[(E, E)-hexa-2,4-dienyloxy]biphenyl

Triphenylphosphine (0.95 g, 0.0036 mol) was added in small portions to a solution of (E, E)-hexa-2,4-dien-1-ol (0.40 g, 0.0040 mol), 4-cyano-4'-hydroxybiphenyl (0.71 g, 0.0036 mol) diethylazodicarboxylate (0.63 g, 0.0036 mol) in dry diethyl ether (40 cm$^3$), cooled in an ice bath under an atmosphere of nitrogen. The reaction mixture was stirred at room temperature overnight. The solvent was removed under reduced pressure and the crude product was purified by column chromatography on silica gel using a 4:1 petroleum (40–60° C.) ether/ethyl acetate mixture as eluent, followed by recrystallisation from ethanol to yield 0.19 g (19%) of the pure ether, K 125° C. N-I 152° C.

The following compounds could be obtained analogously:
4-Cyano-4'-[(E, E)-hepta-2,4-dienyloxy]biphenyl.
4-Cyano-4'-[(E, E)-octa-2,4-dienyloxy]biphenyl.
4-Cyano-4'-[(E, E)-nona-2,4-dienyloxy]biphenyl.
4-Cyano-4'-[(E, E)-deca-2,4-dienyloxy]biphenyl.
4-Fluoro-4'-[(E, E)-hexa-2,4-dienyloxy]biphenyl.
4-Chloro-4'-[(E, E)-hexa-2,4-dienyloxy]biphenyl.
4-Bromo-'-[(E, E)-hexa-2,4-dienyloxy]biphenyl.
3,4-Difluoro-4'-[(E, E)-hexa-2,4-dienyloxy]biphenyl.
3,4,5-Trifluoro-4'-[(E, E)-hexa-2,4-dienyloxy]biphenyl.
4-Trifuoromethoxy-4'-[(E, E,)-hexa-2,4-dienyloxy]biphenyl.
4-Trifluoromethyl-4'-[(E, E)-hexa-2,4-dienyloxy]biphenyl.
4-Trifluoroaceto-4'-[(E, E)-hexa-2,4-dienyloxy]biphenyl.
4-Propyl-4'-[(E, E)-hexa-2,4-dienyloxy]biphenyl.
4-Pentyl-4'-[(E, E)-hexa-2,4-dienyloxy]biphenyl, K 119° C., $S_A$-I 136° C.
4-Heptyl-4'-[(E, E)-hexa-2,4-dienyloxy]biphenyl.
4-Methoxy-4'-[(E, E)-hexa-2,4-dienyloxy]biphenyl.
4-Ethoxy-4'-[(E, E)-hexa-2,4-dienyloxy]biphenyl.
4-Propoxy-4'-[(E, E)-hexa-2,4-dienyloxy]biphenyl.
4-Butoxy-4'-[(E, E)-hexa-2,4-dienyloxy]biphenyl.
4-Pentyloxy-4'-[(E, E)-hexa-2,4-dienyloxy]biphenyl.
4-Hexytoxy-4'-[(E, E)-hexa-2,4-dienyloxy]biphenyl.
4-Heptyloxy-4'-[(E, E)-hexa-2,4-dienyloxy]biphenyl.
4-Octyloxy-4'-[(E, E)-hexa-2,4-dienyloxy]biphenyl.
4-Nonyloxy-4'-[(E, E)-hexa-2,4-dienyloxy]biphenyl.
4-Decyloxy-4'-[(E, E)-hexa-2,4-dienyloxy]biphenyl.
4-[(E)-But-2-enyloxy]-4'-[(E, E)-hexa-2,4-dienyloxy]biphenyl.
4,4'-Di-[(E, E)-hexa-2,4-dienyloxy]biphenyl.
1-(trans-4-Pentylcyclohexyl)-4-[(E, E)-hexa-2,4-dienyloxy]benzene, K 71° C., N-I 107° C.

EXAMPLE 2

Preparation of 4'-Cyanobiphenyl-4-yl (E, E)-hexa-2,4-dienoate

A solution of N, N'-dicyclohexylcarbodiimide (0.87 g, 0.0042 mol) in dichloromethane (10 cm$^3$) was added to a solution of (E, E)-hexa-2,4-dienoic acid (0.47 g, 0.0042 mol), 4-cyano-4'-hydroxybiphenyl (0.67 g, 0.0035 mol), 4-(dimethylamino)pyridine (0.05 g) in dichloromethane (25 cm$^3$), cooled in an ice bath (0° C.) under an atmosphere of nitrogen. The reaction mixture was stirred overnight, filtered to remove precipitated material and the filtrate was evaporated down under reduced pressure. The crude product was purified by column chromatography on silica gel using dichloromethane as eluent, followed by recrystallisation from a 1:1 ethanol/ethyl acetate mixture to yield 0.76 9 (76%). K 160° C., N-I 227° C.

The following compounds could be obtained analogously:

4-Cyanophenyl (E, E)-hexa-2,4-dienoate, K 111° C.
4-Cyanophenyl (E, E)-hepta-2,4-dienoate.
4-Cyanophenyl (E, E)-octa-2,4-dienoate.
2-Cyanonaphthyl-6-yl (E, E)-hexa-2,4-dienoate, K 116° C., N-I 141° C.
2-Cyanonaphthyl-6-yl (E, E)-hepta-2,4-dienoate.
2-Cyanonaphthyl-6-yl (E, E)-octa-2,4-dienoate.
Biphenyl4-yl (E, E)-hexa-2,4-dienoate, K 110° C., $S_A$-N 84° C., N-I 92° C.
Biphenyl-4-yl (E, E)-hepta-2,4-dienoate.
Biphenyl-4-yl (E, E)-octa-2,4-dienoate.
4'-Propylbiphenyl-4-yl (E, E)-hexa-2,4-dienoate.
4'-Pentylbiphenyl-4-yl (E, E)-hexa-2,4-dienoate, K 86° C., N-I 168° C.
4'-Heptylbiphenyl-4-yl (E, E)-hexa-2,4-dienoate.
4'-Propyloxybiphenyl-4-yl (E, E)-hexa-2,4-dienoate.
4'-Butyloxybiphenyl4-yl (E, E)-hexa-2.4-dienoate.
4'-Pentyloxybiphenyl-4-yl (E, E)-hexa-2,4-dienoate.
4'-Hexyloxybiphenyl-4-y(E, E)-hexa-2,4-dienoate.
4'-Heptyloxybiphenyl-4-yl (E, E)-hexa-2,4-dienoate.
4'-Octyloxybiphenyl-4-yl (E, E)-hexa-2,4-dienoate.
4'-(Trifluoromethoxy)biphenyl4-yl (E, E)-hexa-2,4-dienoate.
4'-(Trifluoroaceto)biphenyl4-yl (E, E)-hexa-2,4-dienoate.
4'-Fluorobiphenyl-4-yl (E, E)-hexa-2,4-dienoate.
3',4'-Difluorobiphenyl-4-yl (E, E)-hexa-2,4-dienoate.
3',4',5'-Trifluorobiphenyl-4-yl (E, E)-hexa-2,4-dienoate.
trans-4-Cyanocyclohexyl (E, E)-hepta-2,4-dienoate.
trans-4-Cyanocyclohexyl (E, E)-octa-2,4ienoate.
trans-4-(4'-Cyanophenyl)cyclohexyl (E, E)-hexa-2,4-dienoate.
trans-4-(4'-Fluorophenyl)cyclohexyl (E, E)-hexa-2,4-dienoate.
trans-4-(4'-Trifluoromethoxyphenyl)cyclohexyl (E, E)-hexa-2,4-dienoate.
trans-4-(4'-Trifluoroacetophenyl)cyclohexyl (E, E)-hexa-2,4-dienoate.
4-(trans-4-Cyanocyclohexyl)phenyl (E, E)-hexa-2,4-dienoate.
trans-4-(trans-4-Cyanocyclohexyl)cyclohexyl (E, E)-hexa-2,4-dienoate.
4-(trans-4-Pentylcyclohexyl)phenyl (E, E)-hexa-2,4-dienoate, K 86° C., N-I 172° C.
trans-4-(trans-4-Propylcyclohexyl)cyclohexyl (E, E)-hexa-2,4-dienoate.
trans-4-(trans-4-Pentylcyclohexyl)cyclohexyl (E, E)-hexa-2,4-dienoate, K 117° C., N-I 180°C.
trans-4-(trans-4-Heptylcyclohexyl)cyclohexyl (E, E)-hexa-2,4-dienoate.
trans-4-(trans-4-Propylcyclohexyl)cyclohexyl (E, E)-hepta-2,4dienoate.
trans-4-(trans-4-Pentylcyclohexyl)cyclohexyl (E, E)-hepta-2,4-dienoate.
trans-4-(trans-4-Heptylcyclohexyl)cyclohexyl (E, E)-hepta-2,4-dienoate.
trans-4-(trans-4-Propylcyclohexyl)cyclohexyl (E, E)-octa-2,4-dienoate.
trans-4-(trans-4-Pentylcyclohexyl)cyclohexyl (E, E)-octa-2,4-dienoate.
trans-4-(trans-4-Heptylcyclohexyl)cyclohexyl (E, E)-octa-2,4-dienoate.
t-(trans-4-Propylcyclohexyl)phenyl (E, E)-hexa-2,4-dienoate.
4-(trans-4-Heptylcyclohexyl)phenyl (E, E)-hexa-2,4-dienoate.
4-(trans-4-Propylcyclohexyl)phenyl (E, E)-hepta-2,4-dienoate.
4-(trans-4-Pentylcyclohexyl)phenyl (E, E)-hepta-2,4-dienoate.
4-(trans-4-Heptylcyclohexyl)phenyl (E, E)-hepta-2,4-dienoate.
4-(trans-4-Propylcyclohexyl)phenyl (E, E)-octa-2,4-dienoate.
4-(trans-4-Pentylcyclohexyl)phenyl (E, E)-octa-2,4-dienoate.
4-(trans-4-Heptylcyclohexyl)phenyl (E, E)-octa-2,4-dienoate.
4-(5-Pentylpyrimidin-2-yl)phenyl (E, E)-hexa-2,4-dienoate.
4-(2-Pentylpyridin-5-yl)phenyl (E, E)-hexa-2,4-dienoate.
4-(5-Cyanopyridin-2-yl)phenyl (E, E)-hexa-2,4-dienoate.
4-(2-Cyanopyridin-5-yl)phenyl (E, E)-hexa-2,4-dienoate.
4-(5-Pentylpyridin-2-yl)phenyl (E, E)-hexa-2,4-dienoate.
4-(2-Pentylpyridin-5-yl)phenyl (E, E)-hexa-2,4-dienoate.
4-(5-Cyanopyridin-2-yl)phenyl (E, E)-hexa-2,4-dienoate.
4-(2-Cyanopyridin-5-yl)phenyl (E, E)-hexa-2,4-dienoate.
5-(4-Pentylphenyl)pyrimidin-2-yl (E, E)-hexa-2,4-dienoate.
2-(4-Pentylphenyl)pyrimidin-5-yl (E, E)-hexa-2,4-dienoate.
5-(4-Cyanophenyl)pyrimidin-2-yl (E, E)-hexa-2,4-dienoate.
2-(4-Cyanophenyl)pyrimidin-5-yl (E, E)-hexa-2,4-dienoate.
5-(4-Pentylphenyl)pyridin-2-yl (E, E)-hexa-2,4-dienoate.
2-(4-Pentylphenyl)pyridin-5-yl (E, E)-hexa-2,4-dienoate.
5-(4-Cyanophenyl)pyridin-2-yl (E, E)-hexa-2,4-dienoate.
2-(4-Cyanophenyl)pyridin-5-yl (E, E)-hexa-2,4-dienoate.
4-[(E, E)-hexa-2,4-dienoyloxy]phenyl (E, E)-hexa-2,4-dienoate, K 183° C., N-I 186° C.
4-[(E, E)-hepta-2,4-dienoyloxy]phenyl (E, E)-hepta-2,4-dienoate.
[(E, E)-octa-2,4-dienoyloxy]phenyl (E, E)-octa-2,4-dienoate.
4-(5-Cyanothophen-2-yl)phenyl (E,E)-hexa-2,4-dienoate, K 168° C., N-I 188° C.
4-(5-Pentylthophen-2-yl)phenyl (E,E)-hexa-2,4-dienoate, K 76° C., N-I 125° C.

EXAMPLE 3

Preparation of trans-, trans-4-(E, E)-hexa-2,4-dienyloxy4'-pentyl-1, 1'-bicyclohexane A mixture of toluene-4-sulfonic acid (E, E)-hexa-2,4-dienyl ester (1.0 g, 4.0 mmol), trans-, trans-4-hydroxy-4'- pentyl-1, 1'-bicyclohexane (0.37 g, 1.5 mmol), potassium tert-butoxide (0.55 g, 4.5 mrnol) and 1,2-dimethoxyethane (20 cm$^3$) is stirred at room temperature overnight, filtered to remove inorganic material, diluted with water (100 cm$^3$) and then extracted into diethyl ether (3×25 cm$^3$). The combined organic extracts are washed with water (2×200 cm$^3$), dried (MgSO$_4$), filtered and then evaporated down. The residue is purified by column chromatography on silica gel using a 9:1 hexane/ethyl acetate mixture as eluent and recrystallisation from ethanol to yield 0.25 g (51%) of the desired ether.

The toluene-4-sulfonic acid (E, E)-hexa-2,4-dienyl ester requirets starting material could be prepared as follows:

A solution of toluene4-sulfonyl chloride (0.75 g, 4.0 mmol) in dichloromethane (10 cm$^3$) is added slowly to a solution of (E, E)-hexa-2,4-dienol (0.40 g, 4.0 mmol), triethylamine (0.80 g, 8.0 mmol) and dichloromethane (50 cm$^3$) at 0° C. The reaction mixture is stirred at 0° C. for 6 h, washed with dilute hydrochloric acid (2×50 cm$^3$), water (2×50 cm$^3$) and dilute sodium carbonate solution (2×50 cm$^3$), dried (MgSO4), filtered and then evaporated down to yield 1.0 g (99%) of the desired tosylate, which is used without further purification.

The following compounds could be obtained analogously:

trans-, trans-4-[(E, E)-Hexa-2,4-dienyloxy]-4'-propyl-1, 1'-bicyclohexane.
trans-, trans-4-[(E, E)-Hexa-2,4-dienyloxy]-4'-pentyl-1, 1'-bicyclohexane.
trans-, trans-4-[(E, E)-Hexa-2,4-dienyloxy]-4'-heptyl-1,1'-bicyclohexane.
trans-, trans-4-[(E, E)-Hepta-2,4-dienyloxy]-4'-propyl-1, 1'-bicyclohexane.
trans-, trans-4-[(E, E)-Hepta-2,4-dienyloxy]-4'-pentyl-1, 1'-bicyclohexane.
trans-, trans-4-[(E, E)-Hepta-2,4-dienyloxy]-4'-heptyl-1, 1'-bicyclohexane.
trans-, trans-4-[(E, E)-Octa-2,4-dienyloxy]-4'-propyl-1, 1'-bicyclohexane.
trans-, trans-4-[(E, E)-Octa-2,4-dienyloxy]-4'-pentyl-1,1'-bicyclohexane.
trans-, trans-4-[(E, E)-Octa-2,4-dienyloxy]-4'-heptyl-1,1'-bicyclohexane.
trans-1-[(E, E)-Hexa-2,4-dienyloxy]-4-propylcyclohexane.
trans-1-[(E, E)-Hexa-2,4-dienyloxy]-4-pentylcyclohexane.
trans-1-[(E, E)-Hexa-2,4-dienyloxy]-4-heptylcyclohexane.
trans-, trans-4,4'-di-[(E, E)-Hexa-2,4-dienyloxy]-1,1'-bicyclohexane.
trans-, trans-4,4'-di-[(E, E)-Hepta-2,4-dienyloxy]-1,1'-bicyclohexane.
trans-, trans-4,4'-di-[(E, E)-Octa-2,4-dienyloxy]-1,1'-bicyclohexane.
trans-, 4-[-((E, E)-Hexa-2,4-dienyloxy]cycloxhexane.
trans-4,4 'di-[(E, E)-Hepta-2,4-dienyloxy]cyclohexane.
trans-1, 4di-[(E, E)-Octa-2,4-dienyloxy]cyclohexane.
4-(trans-4-[E, E)-Hexa-2,4-dienyloxy]cyclohexyl) benzonitrile.
4-(trans-4-[E, E)-Hepta-2,4-dienyloxy]cyclohexyl) benzonitrile.
4-(trans-4-[E, E)-Octa-2,4-dienyloxy]cyclohexyl) benzonitrile.
1-Fluoro-4-(trans-4-[E, E)-hexa-2,4-dienyloxy] cyclohexyl)benzene.
1-Chloro-4-(trans-4-[E, E)-hexa-2,4-dienyloxy] cyclohexyl)benzene.
1-Bromo-4-(trans-4-[E, E)-hexa-2,4-dienyloxy] cyclohexyl)benzene.
1,2-Difluoro-4-(trans-4-[E, E)-hexa-2,4-dienyloxy] cyclohexyl)benzene.
1,2,6-Trifluoro-4-(trans-4-[E, E)-hexa-2,4-dienyloxy] cyclohexyl)benzene.
1-Trifluoromethoxy-4-(trans-4-[E, E)-hexa-2,4-dienyloxy]cyclohexyl)benzene.
1-Trifluoromethyl-4-(trans-4-[E, E)-hexa-2,4dienyloxy] cyclohexyl)benzene.
1-Trifluoroaceto-4-(trans-4-[E, E)-hexa-2,4-dienyloxy] cyclohexyl)benzene.
1-Propyl-4-(trans-4-[E, E)-hexa-2,4dienyloxy] cyclohexyl)benzene.
1-Pentyl-4-(trans-4-[E, E)-hexa-2,4-dienyloxy] cyclohexyl)benzene.
1-Heptyl-4-(trans-4-[E, E)-hexa-2,4-dienyloxy] cyclohexyl)benzene.
1-Methoxy-4-(trans-4-[E, E)-hexa-2,4-dienyloxy] cyclohexyl)benzene.
1-Ethoxy-4-(trans-4-[E, E)-hexa-2,4-dienyloxy] cyclohexyl)benzene.
1-Proxy-4-(trans-4-[E, E)-hexa-2,4-dienyloxy] cycohexyl)benzene.
1-Butoxy-4-(trans-4-[E, E)-hexa-2,4-dienyloxy] cyclohexyl)benzene.
1-Pentyloxy-4-(trans-4-[E, E)-hexa-2,4-dienyloxy] cyclohexyl)benzene.
1-Hexyloxy-4-(trans-4-[E, E)-hexa-2,4-dienyloxy] cyclohexyl)benzene.
1-Heptyloxy-4-(trans-4-[E, E)-hexa-2,4-dienyloxy] cyclohexyl)benzene.
1-Octyloxy-4-(trans-4-[E, E)-hexa-2,4-dienyloxy] cyclohexyl)benzene.
4-Cyano-4'-(trans-4-[E, E)-hexa-2,4-dienyloxy] cyclohexyl)biphenyl.
4-Fluoro-4-(trans 4-[E, E)-hexa-2,4-dienyloxy] cyclohexyl)biphenyl.
4-Chloro-4'-(trans-4-[E, E)-hexa-2,4-dienyloxy] cyclohexyl)biphenyl.
4-Bromo-4'-(trans-4-[E, E)-hexa-2,4-dienyloxy[]cyclohexyl)biphenyl.
4-Trifluoromethoxy-4'-(trans-4-[E, E)-hexa-2, 4dienyloxy]cyclohexyl)biphenyl.
4-Trifluoromethyl-4'-(trans-4-[E, E)-hexa-2,4dienyloxy] cyclohexyl)biphenyl.
4-Propyl-4'-(trans-4-[E, E)-hexa-2,4-dienyloxy] cyclohexyl)biphenyl.
4-Pentyl-4'-(trans-4-[E, E)-hexa-2,4-dienyloxy] cyclohexyl)biphenyl.
4-Heptyl-4'-(trans-4-4E, E)-hexa-2,4dienyoxy] cyclohexyl)bipheyenyl.
4-Methoxy-4'-(trans-4-[E, E)-hexa-2,4-dienyloxy] cyclohexyl)biphenyl.
4-Ethoxy-4'-(trans-4-[E, E)-hexa-2,4-dienyloxy] cyclohexyl)biphenyl.
4-Propoxy-4'-(trans-4-[E, E)-hexa-2,4-dienyloxy] cyclohexyl)biphenyl.
4-Butoxy-4'-(trans-4-[E, E)-hexa-2,4-dienyloxy] cyclohexyl)biphenyl.

4-Pentyloxy-4'-(trans-4-[E, E)-hexa-2,4-dienyloxy]cyclohexyl)biphenyl.
4-Hexyloxy-4'-(trans-4-[E, E)-hexa-2,4-dienyloxy]cyclohexyl)biphehyl.
4-Heptyoxy-4'-(trans-4-[E, E)-hexa-2,4-dienyloxy]cyclohexyl)biphenyl.
4-[trans-4-(trans-4-[(E, E)-Hexa-2,4-dienyloxy]cyclohexyl)cyclohexyl]benzonitrile.
1-Fluoro-4-[trans-4-(trans-[(E, E)-hexa-2,4-dienyloxy]cyclohexyl)cyclohexyl]benzene.
1-Chloro-4-[trans-4-(trans-4-[(E, E)-hexa-2,4-dienyloxy]cyclohexy]cyclohexyl)benzene.
1-Chomro-4-[trans-4-(trans-4-[(E, E)-hexa-2,4-dienyloxy]cyclohexyl]cyclohexyl)benzene.
1-Trifluoromethoxy-4-[trans-4-(trans-4-[(E, E)-hexa-2,4-dienyloxy]cyclohexyl)cyclohexyl]benzene.
1-Trifluoromethyl-4-[trans-4-(trans-4-[(E, E)-hexa-2,4-dienyloxy]cyclohexyl)cyclohexyl]benzene.
1-Trifluoroaceto-4-[trans-4-(trans-4-[(E, E)-hexa-2,4-dienyloxy]cyclohexyl)cyclohexyl]benzene.
4-(trans-5-[E, E)-Hexa-2,4-dienyloxy]dioxan-2-yl)benzonitrile.
4-(trans-5-[E, E)-Hepta-2,4-dienyloxy]dioxan-2-yl)benzonitrile.
4-(trans-5-[E, E)-Octa-2,4-dienyloxy]dioxan-2-yl)benzonitrile.
1-Fluoro-4-(trans-5-[E, E)-hexa-2,4-dienyloxyl]dioxan-2-yl)benzene.
1-Chloro-4-(trans-5-[E, E)-hexa-2,4dienyloxy]dioxan-2-yl)benzene.
1-Bromo-4-(trans-5-[E, E)-hexa-2,4-dienyloxy]dioxan-2-yl)benzene.
1,2-Difluoro-4-(trans-5-[E, E)-hexa-2-dienyloxy-]dioxan-2-yl)benzene.
1,2,6-Trifluoro-4-(trans-5-[E, E)-hexa-2,4dienyloxyl]dioxan-2-yl)benzene.
1-Trifluoromethoxy-4-(trans -5-[E, E)-hexa-2,4-dienyloxy]dioxan-2-yl)benzene.
1-Trifluoromethyl-4-(trans-5-[E, E)-hexa-2,4dienyloxyl]dioxan-2-yl)benzene.
1-Trifluoroaceto-4-(trans-5-[E, E)-hexa-2,4dienyloxy]dioxan-2-yl)benzene.
1-Propyl-4-(trans-5-[E, E)-hexa-2,4dienyloxy]dioxan-2-yl)benzene.
1-Pentyl-(trans-5-[E, E)-hexa-2,4dienyloxy]dioxan-2-yl)benzene.
1-Heptyl-4-(trans-5-[E, E)-hexa-2,4dienyloxyl]dioxan-2-yl)benzene.
1-Methoxy-4-(trans-5-[E, E)-hexa-2,4dienyloxy]dioxan-2-yl)benzene.
1-Ethoxy-4-(trans-5-[E, E)-hexa-2,4dienyloxy]dioxan-2-yl)benzene.
1-Proxy-4-(trans-5-[E, E)-hexa-2,4dienyloxy]dioxan-2-yl)benzene.
1-Butxyl-4-(trans-5-[E, E)-hexa-2,4dienyloxy]dioxan-2-yl)benzene.
1-Pentyloxy-4-(trans-5-[E, E)-hexa-2,4-dienyloxy]dioxan-2-yl)benzene.
1-Hexyloxy-4-(trans-5-[E, E)-hexa-2,4-dienyloxy]dioxan-2-yl)benzene.
1-Heptyloxy-4-(trans-5-[E, E)-hexa-2,4-dienyloxy]dioxan-2-yl)benzene.
1-Octyloxy-4-(trans-5-[E, E)-hexa-2,4-dienyloxy]dioxan-2-yl)benzene.
1-Cyano-4'-(trans-5-[E, E)-hexa-2,4-dienyloxy]dioxan-2-yl)biphenyl.
4-Fluoro-4'-(trans-5-[E, E)-hexa-2,4-dienyloxy]dioxan-2-yl)biphenyl.
4-Chloro-4'-(trans-5-[E, E)-hexa-2,4-dienyloxy]dioxan-2-yl)biphenyl.
4-Bromo-4'-(trans-5-[E, E)-hexa-2,4-dienyloxy]dioxan-2-yl)biphenyl.
4-Trifluoromethoxy-4'-(trans-5-[E, E)-hexa-2,4-dienyloxy]dioxan-2-yl)biphenyl.
4-Trifluoromethyl-4'-(trans-5-[E, E)-hexa-2,4-dienyloxy]dioxan-2-yl)biphenyl.
4-Propyl-4'-(trans-5-[E, E)-hexa-2,4-dienyloxy]dioxan-2-yl)biphenyl.
4-Pentyl-4'-(trans-5-[E, E)-hexa-2,4-dienyloxy]dioxan-2-yl l)biphenyl.
4-Heptyl-4'-(trans-5-[E, E)-hexa-2,4dienyloxy]dioxan-2-yl)biphenyl.
4-Methoxy-4'-(trans-5-[E, E)-hexa-2,4dienyloxy]dioxan-2-yl)biphenyl.
4-Ethoxy-4'-(trans-5-[E, E)-hexa-2,4-dienyloxy]dioxan-2-yl)biphenyl.
4-Propoxy-4'-(trans-5-[E, E)-hexa-2,4-dienyloxy]dioxan-2-yl)biphenyl.
4-Butoxy-4'-(trans-5-[E, E)-hexa-2,4-dienyloxy]dioxan-2-yl)biphenyl.
4-Pentyloxy-4'-(trans-5-[E, E)-hexa-2,4-dienyloxy]dioxan-2-yl)biphenyl.
4-Hexyloxy-4'-(trans-5-[E, E)-hexa-2,4-dienyloxy)]dioxan-2-yl)biphenyl.
4-Heptyloxy4'-(trans-5-[E, E)-hexa-2,4-dienyloxy]dioxan-2-yl)biphenyl.
4-[trans-4-(trans-5-[(E, E)-Hexa-2,4-dienyloxy]dioxan-2-yl)cyclohexyl]benzonitrile.

TABLE 1

Transition temperatures for the compounds below:

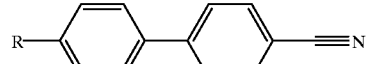

| Compound | R | C-N/° C. | N-I/° C. | ΔT$_{NI}$/° C. |
|---|---|---|---|---|
| | 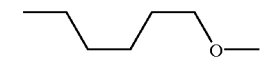 | 58 | 77 | 19 |
| (E) |  | 74 | 82 | 8 |
| (E) | 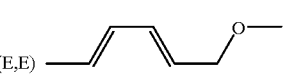 | 74 | 81 | 7 |
| (E,E) | | 125 | 152 | 27 |

TABLE 2

Transition temperatures for the compounds below:

| Compound (R) | C-N/° C. | N-I/° C. | ΔT$_{NI}$/° C. |
|---|---|---|---|
| (E) [structure] | 53 | 71 | 18 |
| (E) [structure] | 92 | 131 | 39 |
| (E) [structure] | 97 | (74) | — |
| (E,E) [structure] | 160 | 227 | 67 |

TABLE 3

Transition temperatures for the compounds below

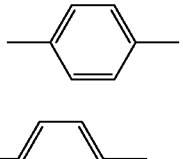

| Compound X | C-N/° C. | S$_A$-N/° C. | N-I/° C. | ΔT$_{NI}$/° C. |
|---|---|---|---|---|
| H | 110 | (84) | (92) | — |
| CN | 160 | — | 227 | 67 |

( ) Represents a monotropic transition temperature ( ) Represents a monotropic transition temperature

TABLE 4

Transition temperatures for the compounds below

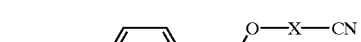

| Compound X | C-N/I ° C. | N-I/° C. | ΔT$_{NI}$/° C. |
|---|---|---|---|
| [phenyl] | 111 | — | — |
| [naphthyl] | 116 | 141 | 27 |

TABLE 4-continued

Transition temperatures for the compounds below

| Compound X | C-N/I ° C. | N-I/° C. | ΔT$_{NI}$/° C. |
|---|---|---|---|
| [biphenyl] | 160 | 227 | 67 |

TABLE 5

Transition temperatures for the compounds below

| Compound Z$_1$ | Z$_2$ | C-N/I/° C. | N-I | ΔT$_{NI}$/° C. |
|---|---|---|---|---|
| OOC | COO | 86 | — | — |
| COO | OOC | 183 | 186 | 3 |

TABLE 6

Transition temperatures for the compounds

| Compound R | C-N/° C. | N-I/° C. |
|---|---|---|
| [phenyl-phenyl] | 86 | 172 |
| [cyclohexyl] | 117 | 180 |

The following birefringence data was obtained:

Wt/% in ZLI3086=5
Ext Δn 30° C.=0.328
Ext Δn 20° C.=0.333
Ext Δn T/T$_{NI}$=0.8=0.298 wherein Ext Δn is a linar extrapolation in concentration of the birefringence in ZLI3086 which is a commercially available (from Merck UK) apolar nematic host mixture. T is the temperature at which the measurement was taken (in Kelvin) and T$_{NI}$ is the phase transition for the nematic-isotropic phase change (in Kelvin).

One known device in which the materials of the current invention may be incorporated is the twisted nematic device which uses a thin layer of a nematic material between glass slides. The slides are unidirectionally rubbed and assembled with the rubbing directions orthogonal. The rubbing gives a surface alignment to the liquid crystal molecules resulting in a progressive 90° twist across the layer. When placed between polarisers, with their optical axis perpendicular or parallel to a rubbing direction the device rotates the plane of polarised light in its OFF state and transmits without rotation in the ON state. Small amounts of cholesteric material may be added to the nematic material to ensure the 90° twist is of the same sense across the whole area of the device as explained in UK patents 1,472,247 and 1,478,592.

An improvement in the performance of large, complex, nematic LCDs occurred in 1982 when it was observed that the voltage dependence of the transmission of nematic LC layers with twist angles in the range 180° to 270° could become infinitely steep, see C. M. Waters, V. Brimmell and E. P. Raynes, Proc. 3rd Int. Display Res. Conf., Kobe, Japan, 1983, 396. The largertwist angles are produced by a combination of surface alignment and making the nematic mixture into a long pitch cholesteric by the addition of a small amount of a chiral twisting agent. The increasing twist angle steepens the transmission/voltage curve, until it becomes bistable for 270° twist; for a specific twist angle between 225° and 270° the curve becomes infinitely steep and well suited to multiplexing. The larger twist angles present have resulted in the name supertwisted nematic (STN) for these LCDs.

Liquid Crystal Devices describing the use of STNs may be found in patent application GB 8218821 and resulting granted patents including U.S. Pat. No. 4,596,446.

Figure 2:
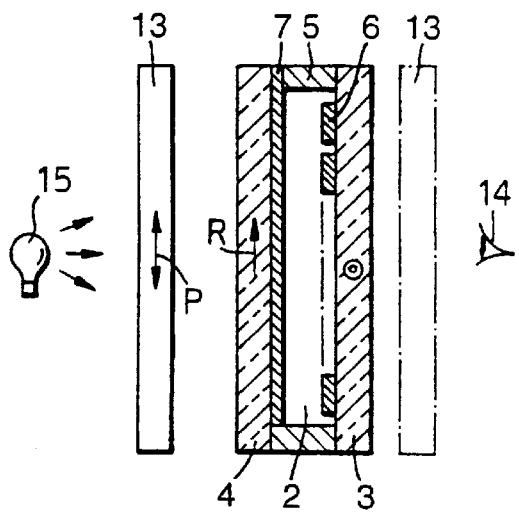
FIG. 2 is a cross-section of a display such as that of FIG. 1 in a transmission mode.
Figure 3:
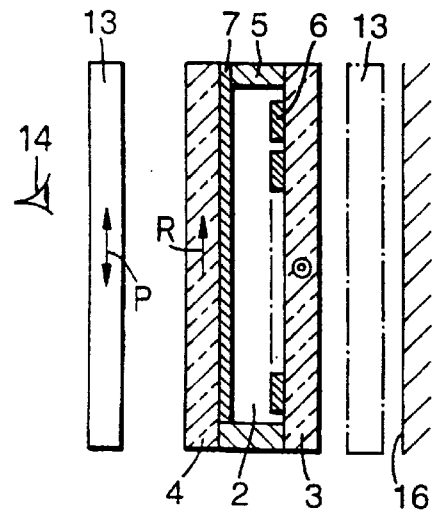
FIG. 3 is a cross-section of a display similar to FIG. 2 operating in a reflective mode.

The display of FIGS. 1 and 2 comprises a liquid crystal cell 1 formed by a layer 2 of cholesteric liquid crystal material contained between glass walls 3,4. A spacer ring 5 maintains the walls typically 6 $\mu$m apart. Strip like row electrodes $6_1$ to $6_m$, e.g. of $SnO_2$ are formed on one wall 3 and similar column electrodes $7_1$ to $7_n$ formed on the other wall 4. With m-row electrodes and n-column electrodes this forms an mxn matrix of addressable elements. Each element is formed by the interaction of a row and column electrode.

A row driver supplies voltage to each row electrode 6. Similarly a column drive 9 supplies voltages to each column electrode 7. Control of applied voltages is from a control logic 10 which receives power from a voltage source 11 and timing from a clock 12.

An example of the use of a material and device embodying the present invention will now be described with reference to FIG. 2.

The liquid crystal device consists of two transparent plates, 3 and 4, for example made from glass. These plates are coated on their internal face with transparent conducting electrodes 6 and 7. An alignment layer is introduced onto the internal faces of the cell so that a planar orientation of the molecules making up the liquid crystalline material will be approximately parallel to the glass plates 3 and 4. This is done by coating the glass plates 3,4 complete with conducting electrodes so that the intersections between each column and row form an x, y matrix of addressable elements or pixels. For some types of display the alignment directions are orthogonal. Prior to the construction of the cell the alignment layers are rubbed with a roller covered in cloth (for example made from velvet) in a given direction, the rubbing directions being arranged parallel (same or opposite direction) upon construction of the cell. A spacer 5 e.g. of polymethyl methacrylate separates the glass plates 3 and 4 to a suitable distance e.g. 2 microns. Liquid crystal material 2 is introduced between glass plates 3,4 by filling the space in between them. This may be done by flow filling the cell using standard techniques. The spacer 5 is sealed with an adhesive in a vacuum using an existing technique. Polarisers 13 may be arranged in front of and behind the cell.

Alignment layers may be introduced onto one or more of the cell walls by one or more of the standard surface treatment techniques such as rubbing, oblique evaporation or as described above by the use of polymer aligning layers.

In alternative embodiments the substrates with the aligning layers on them are heated and sheared to induce alignment, alternatively the substrates with the aligning layers are thermally annealed above the glass transition temperature and below the liquid crystal to isotropic phase transition in combination with an applied field. Further embodiments may involve a combination of these aligning techniques. With some of these combinations an alignment layer may not be necessary.

The device may operate in a transmissive or reflective mode. In the former, light passing through the device, e.g. from a tungsten bulb, is selectively transmitted or blocked to form the desired display. In the reflective mode a mirror, or diffuse reflector, (16) is placed behind the second polariser 13 to reflect ambient light back through the cell and two polarisers. By making the mirror partly reflecting the device may be operated both in a transmissive and reflective mode.

The alignment layers have two functions, one to align contacting liquid crystal molecules in a preferred direction and the other to give a tilt to these molecules—a so called surface tilt—of a few degrees typically around 4° or 5°. The alignment layers may be formed by placing a few drops of the polyimide on to the cell wall and spinning the wall until a uniform thickness is obtained. The polyimide is then cured by heating to a predetermined temperature for a predetermined time followed by unidirectional rubbing with a roller coated with a nylon cloth.

In an alternative embodiment a single polariser and dye material may be combined.

Cholesteric or chiral nematic liquid crystals possess a twisted helical structure which is capable of responding to a temperature change through a change in the helical pitch length. Therefore as the temperature is changed then the wavelength of the light reflected from the planar cholesteric structure will change and if the reflected light covers the visible range then distinct changes in colour occur as the temperature varies. This means that there are many possible applications including the areas of thermography and thermooptics.

The cholesteric mesophase differs from the nematic phase in that in the cholesteric phase the director is not constant in space but undergoes a helical distortion. The pitch length for the helix is a measure of the distance for the director to turn through 3600.

By definition, a cholesteric material is chiral material. Cholesteric materials may also be used in electro-optical displays as dopants, for example in twisted nematic displays where they may be used to remove reverse twist defects, they may also be used in cholesteric to nematic dyed phase change displays where they may be used to enhance contrast by preventing waveguiding.

Thermochromic applications of cholesteric liquid crystal materials usually use thin film preparations of the cholesterogen which are then viewed against a black background. These temperature sensing devices may be placed into a number of applications involving thermometry, medical thermography, non-destructive testing, radiation sensing and for decorative purposes. Examples of these may be found in D G McDonnell in Thermotropic Liquid Crystals, Critical Reports on Applied Chemistry, Vol 22, edited by G W Gray, 1987 pp 120–44; this reference also contains a general description of thermochromic cholesteric liquid crystals.

Generally, commercial thermochromic applications require the formulation of mixtures which possess low melting points, short pitch lengths and smectic transitions just below the required temperature-sensing region. Preferably the mixture or material should retain a low melting point and high smectic-cholesteric transition temperatures.

In general, thermochromic liquid crystal devices have a thin film of cholesterogen sandwiched between a transparent supporting substrate and a black absorbing layer. One of the fabrication methods involves producing an 'ink' with the liquid crystal by encapsulating it in a polymer and using printing technologies to apply it to the supporting substrate. Methods of manufacturing the inks include gelatin microencapsulation, U.S. Pat. No. 3,585,318 and polymer dispersion, U.S. Pat. Nos. 1,161,039 and 3,872,050. One of the ways for preparing well-aligned thin-film structures of cholesteric liquid crystals involves laminating the liquid crystal between two embossed plastic sheets. This technique is described in UK patent 2,143,323.

For a review of thermochromism in liquid crystals see J G Grabmaier in 'Applications of Liquid Crystals', G Meier, E Sackmann and J G Grabmaier, Springer-Verlag, Berlin and New York, 1975, pp 83–158.

The materials of the current invention may be used in many of the known devices including those mentioned in the introduction.

What is claimed is:

1. A compound of formula I

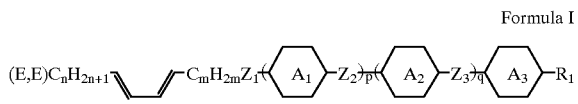

Formula I wherein n is 1–5;

m is 0–5;

p is 0, 1 or 2;

q is 0, 1 or 2 p+q is less than or equal to 3;

$A_1$, $A_2$, $A_3$ are independently chosen from 1,4-disubstituted benzene, 2,5-disubstituted pyrimidine, 2,5-disubstituted pyridine, 2,6-disubstituted naphthalene which may be laterally substituted with F, Cl, Br or CN, trans-4-disubstituted cyclohexane, 2,5-disubstituted dioxane, 2,5-disubstituted thiophene, 2,5-disubstituted furan, and 2,5-disubstituted thiodiazole;

$Z_1$ may be COO, OOC, $OCH_2$ or O;

$Z_2$, $Z_3$ are independently chosen from a direct bond, COO, OOC, $C_2H_4$, $CH_2O$, $OCH_2$, $C_4H_8$, $C_3H_6O$, (E)—CH=CH$C_2H_4$, (E)—CH=CH$CH_2$O or —C≡C—; and $R_1$ is alkyl, and may contain up to 20 carbon atoms and may be branched or a straight chain;

provided that at least one of, $A_1$, $A_2$, $A_3$ is selected from 2,5-disubstituted thiophene.

2. A compound according to claim 1 wherein:

n is 1–3;

when $Z_1$ is 0 m is 1 and when $Z_1$ is COO m is 0;

p is 0 or 1;

q is 0 or 1;

p+q is 0 or 1;

$A_1$, $A_2$, $A_3$, are 1,4-disubstituted benzene or trans-1,4-disubstituted cyclohexane; and $Z_2$, $Z_3$ are direct bonds or $C_2H_4$.

3. A compound according to claim 2 wherein n+m is ≦5.

4. A liquid crystal mixture comprising at least one of the compounds according to claim 1.

5. A liquid crystal mixture according to claim 4 wherein the mixture is a nematic liquid crystal mixture.

6. A liquid crystal mixture according to claim 4 wherein the mixture is a cholesteric liquid crystal mixture.

7. A device comprising two spaced cell walls each bearing electrode structures and treated on at least one facing surface with an alignment layer, a layer of a liquid crystal material enclosed between the cell walls, characterised in that it incorporates the liquid crystal mixture as claimed in claim 4.

8. A device according to claim 7 wherein the device is a twisted nematic device.

9. A device according to claim 7 wherein the device is a super-twisted nematic device.

* * * * *